United States Patent
Aykac et al.

(10) Patent No.: US 11,002,867 B1
(45) Date of Patent: May 11, 2021

(54) DETERMINATION OF CRYSTAL SINGLES RATES TO ESTIMATE MEAN RANDOM COINCIDENCE RATE

(71) Applicant: Siemens Medical Solutions USA, Inc., Malvern, PA (US)

(72) Inventors: Mehmet Aykac, Knoxville, TN (US); Vladimir Y. Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 68 days.

(21) Appl. No.: 16/661,207

(22) Filed: Oct. 23, 2019

(51) Int. Cl.
| | | |
|---|---|---|
| *G01T 1/29* | (2006.01) | |
| *G01T 1/172* | (2006.01) | |
| *G01T 1/202* | (2006.01) | |
| *G06T 7/00* | (2017.01) | |
| *G06T 11/00* | (2006.01) | |
| *G06T 5/00* | (2006.01) | |
| *A61B 6/03* | (2006.01) | |

(52) U.S. Cl.
CPC ............ *G01T 1/2985* (2013.01); *A61B 6/037* (2013.01); *G01T 1/172* (2013.01); *G01T 1/202* (2013.01); *G06T 5/002* (2013.01); *G06T 7/0012* (2013.01); *G06T 11/005* (2013.01); *G06T 2207/10104* (2013.01)

(58) Field of Classification Search
CPC ....... G01T 1/2985; G01T 1/172; G01T 1/202; G06T 7/0012; G06T 2207/10104; G06T 5/037; G06T 11/005; A61B 6/037
See application file for complete search history.

(56) References Cited

U.S. PATENT DOCUMENTS

2017/0371046 A1* 12/2017 Laurence ................ G01T 1/249

OTHER PUBLICATIONS

Oliver & Rafecas. "Modelling Random Coincidences in Positron Emission Tomography by Using Singles and Prompts: A Comparison Study". PLOS One | DOI:10.1371/journal.pone.0162096, Sep. 7, 2016.*

Defrise, M. et al. "A normalization technique for 3D PET data", Phys. Med. Biol., 1991, vol. 36, No. 7, 14pp.

(Continued)

*Primary Examiner* — Michael C Bryant

(57) ABSTRACT

Systems and methods to determine random coincidence rates include determination of a detector rate for each of a plurality of detectors of a positron emission tomography scanner based on a frame of positron emission tomography data, determination of a sensitivity for each detector crystal of the plurality of detectors, based on the detector rate of the detector including the detector crystal, determination of a singles rate for each detector crystal based on the detector rate of the detector including the detector crystal and the determined sensitivity of the detector crystal, estimation of a mean random coincidence rate for each of a plurality of pairs of the detector crystals based on the singles rate of each detector crystal of each of the plurality of pairs of the detector crystals, correction of the acquired frame of positron emission tomography data based on the estimated mean random coincidence rates, and reconstruction of a positron emission tomography image based on the corrected frame of positron emission tomography data.

20 Claims, 12 Drawing Sheets

(56) References Cited

OTHER PUBLICATIONS

Badawi, R.D., et al. "Randoms variance reduction in 3D PET", Phys. Med. Biol., 1999, 14pp.
Rokitta, O. et al. "Random Correction for Positron Emission Tomography Using Singles Count Rates", IEEE, 2001, 4pp.
Stearns, Charles W. et al, Randon Coincidence Estimation from Single Event Rates on the Discovery ST PET/CT Scanner, IEEE 2004, 3pp.
Panin, V. Y. et al. "Simultaneous update iterative algorithm for variance reduction on random coincidences in PET," 2007 IEEE Nuclear Sciences Symposium Conference Record, 5pp.
Stearns, Charles W. et al. "Randoms from Singles Estimation for Long PET Scans", 2011 IEEE Nuclear Science Symposium Conference Record, MIC18.M-98, 3pp.

\* cited by examiner

DETERMINATION OF CRYSTAL SINGLES RATES TO ESTIMATE MEAN RANDOM COINCIDENCE RATE

BACKGROUND

According to conventional positron-emission-tomography (PET) imaging, a radiopharmaceutical tracer is introduced into a patient body typically via radial arterial injection. Radioactive decay of the tracer generates positrons which eventually encounter electrons and are annihilated thereby. Annihilation produces two photons which travel in approximately opposite directions. A ring of detectors surrounding the body detects the emitted photons and reconstructs PET images based thereon.

A "coincidence" is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred.

A "true" coincidence represents the detection of two coincident photons which arose from a single annihilation event located on a LOR between the two detectors. A "random" coincidence represents two coincident photons which did not arise from the same annihilation event. A "scatter" coincidence is a type of true coincidence in which two coincident photons originated from the same annihilation event but the annihilation event was not located along the LOR of the two detectors because one or both of the photons interacted and scattered within the body or media. Since only the true unscattered coincidences indicate locations of annihilation events, random coincidences and scatter coincidences should be subtracted from or otherwise used to correct acquired PET data reconstruction of a PET image.

Conventional PET scanners detect all coincidences without regard to whether the coincidences are true, random or scatter coincidences. Software and/or hardware-based approaches can be used to estimate random coincidences and to subtract the random coincidences from the detected coincidences. For example, one current hardware-based approach involves delaying one of the detected singles events. Undelayed logic detects all coincidences along all LORs as described above. Additional delayed logic delays one input channel by, for example, a few tens of nanoseconds (e.g., 5× the coincidence window) and then performs coincidence detection. As a result, the delayed logic does not detect any actually-true coincidences as coincident. To correct for random coincidences, and along each LOR, the coincidences detected by the delayed logic are subtracted from those detected by the undelayed logic.

Direct subtraction of the random coincidences increases statistical noise due to the statistical variation of each detector pair. Moreover, duplication of the coincidence detection by the coincidence detection components limits the count rate capability of a scanner, particularly in high-activity PET studies. Systems are desired to efficiently correct acquired coincidences data for the presence of random coincidences.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments provide an estimation of a mean random coincidence rate for a pair of detector crystals. The mean random coincidence rate for a pair of detector crystals may be estimated by estimating the crystal singles rate of each crystal of the pair, using the formula $R_{ij}=2\tau s_i s_j$, where $R_{ij}$ is the mean rate of random coincidences for a given pair of crystals i, j, $s_i$ and $s_j$ are the singles rate for each crystal and $\tau$ is the coincidence time window. The mean random coincidence rate for a pair of crystals may then be used to correct the coincidences detected by the pair of crystals as is known in the art.

According to some embodiments, a baseline sensitivity and a rate-dependent sensitivity ratio for each detector crystal are determined based on calibration PET frames and are pre-stored. A subject to be imaged is then scanned, producing a frame of PET data which also specifies a count rate for each detector. A singles rate for the crystals of each detector is then determined based on the count rate, the pre-stored baseline sensitivity of each crystal of the detector and the pre-stored rate-dependent sensitivity ratio rate of each crystal of the detector. Using the formula above, the mean random coincidence rate for each pair of detector crystals may then be determined and used to correct the coincidences of the frame of PET data which were detected by the pairs of detector crystals.

Embodiments may therefore reduce the need to estimate random coincidences using delay logic in the coincidence firmware. Embodiments may also or alternatively increase the count rate capability of PET scanner electronics significantly at high activity levels.

Figure 1:
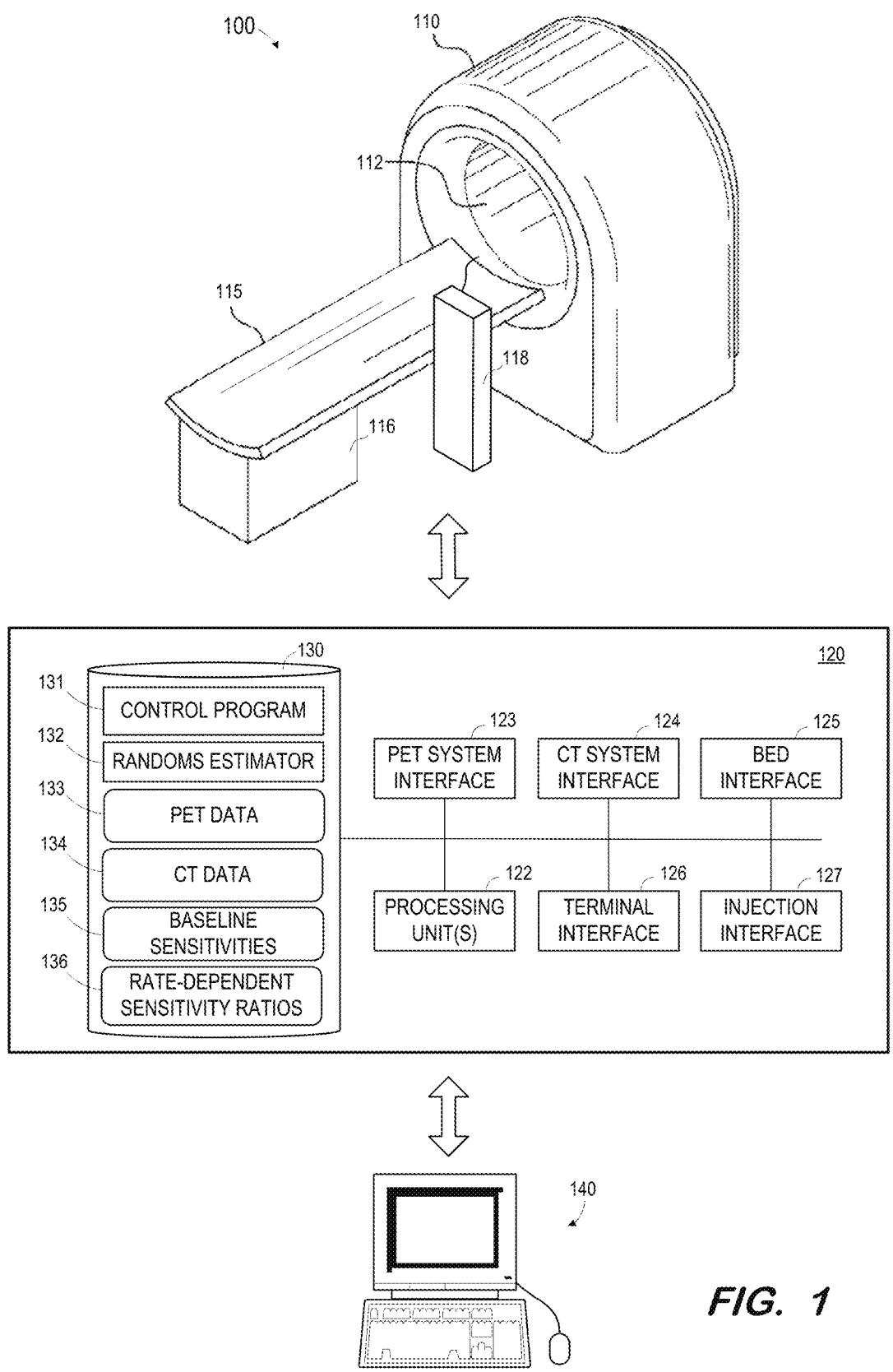
FIG. 1 is a block diagram of a PET/CT imaging system according to some embodiments.

FIG. 1 illustrates PET/CT system 100 to execute one or more of the processes described herein. Embodiments are not limited to system 100.

System 100 includes gantry 110 defining bore 112. As is known in the art, gantry 110 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors in any configuration as is known in the art. Generally, a detector includes one or more scintillation elements and one or more electrical transducers. The scintillation elements create photons with the energy of few electron volts (eV) in response to receiving the 511 keV photons which result from annihilation events. Lutetium oxyorthosilicate (LSO) and lutetium yttrium oxyorthosilicate (LYSO) scintillators exhibit suitable stopping power and fast scintillation decay, and may be used in high count rate scenarios.

The electrical transducers convert the low-energy photons created by the scintillation elements to electrical signals. According to some embodiments, the electrical transducers may comprise silicon photo-multipliers (SiPM) or photo-multiplier tubes (PMT)). Some embodiments employ a block detector which includes more scintillation elements than electrical transducers. In a block detector, multiple electrical transducers receive spread-out low-energy photons resulting from absorption of one of the 511 keV annihilation-generated photons. The relative outputs of the transducers are compared in order to determine the absorption location, which in turn identifies the scintillation element, or crystal, which is determined to have received the annihilation photon. Construction of a block detector, and of rings of block detectors within gantry 110, according to some embodiments will be described in more detail below.

Injection system 118 may operate to deliver calibrated injections of fluorodeoxyglucose (FDG), iodine, or other radiopharmaceuticals to a patient before and/or during a PET scan. In some embodiments, injection system 118 is incorporated into gantry 110. Injection system 118 may support a wired or wireless communications link with control system 120 for receiving information specifying dosage, injection protocol and scan delay.

Bed 115 and base 116 are operable to move a patient lying on bed 115 into and out of bore 112 before, during and after imaging. In some embodiments, bed 115 is configured to translate over base 116 and, in other embodiments, base 116 is movable along with or alternatively from bed 115.

Movement of a patient into and out of bore 112 may allow scanning of the patient using the CT imaging elements and the PET imaging elements of gantry 110. Such scanning may proceed based on scanning parameters such as scan ranges and corresponding scanning speeds. Bed 115 and base 116 may provide continuous bed motion and/or step-and-shoot motion during such scanning according to some embodiments.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with PET system interface 123, bed interface 125, and injection interface 127, control hardware elements to inject a radiopharmaceutical into a patient, move the patient into bore 112 past PET detectors of gantry 110, and detect coincidence events occurring within the patient. The detected events may be stored in memory 130 as PET data 133, which may comprise raw (i.e., list-mode) and/or sinograms. List-mode data may represent each annihilation event using data specifying an LOR and the time at which the event occurred. Time-of-flight (TOF) PET additionally measures the difference between the detection times of the two 511 keV photons arising from the annihilation event. This difference may be used to more accurately estimate a particular position along the LOR at which the annihilation event occurred.

A sinogram is a data array of the angle versus the displacement of each LOR. A sinogram includes one row containing the LOR for a particular azimuthal angle cp. Each of these rows corresponds to a one-dimensional parallel projection of the tracer distribution at a different coordinate. A sinogram stores the location of the LOR of each coincidence such that all the LORs passing through a single point in the volume trace a sinusoid curve in the sinogram.

One or more processing units 122 may also execute control program 131 to, in conjunction with CT system interface 124, cause a radiation source within gantry 110 to emit radiation toward a body within bore 112 from different projection angles, and to control a corresponding detector to acquire two-dimensional CT data. The CT data may be acquired substantially contemporaneously with the PET data as described above, and may be stored as CT data 134. Such CT data 134 may be used for attenuation correction of contemporaneously-acquired PET data 133 as is known in the art. In this regard, control program 131 may also be executed to reconstruct PET data 133 of a PET scan into three-dimensional slices using any reconstruction algorithm that is or becomes known.

Storage device 130 also includes randoms estimator program 132 for estimating mean random coincidence rates for a plurality of scintillation crystal pairs according to some embodiments. As mentioned above and described in detail below, such estimation utilizes previously-acquired baseline sensitivities 135 and rate-dependent sensitivity ratios 136. Baseline sensitivities 135 and rate-dependent sensitivity ratios 136 may be implemented using look-up tables in some embodiments. The look-up tables may be keyed to identifiers of individual detector crystals within gantry 110.

PET images, CT images and/or estimated mean random coincidence rates may be transmitted to terminal 140 via terminal interface 126. Terminal 140 may comprise a display device and an input device coupled to system 120. Terminal 140 may display the PET images, CT images, and/or estimated random coincidence rates. Terminal 140 may receive user input for controlling display of the data, operation of system 100, and/or the processing described herein. In some embodiments, terminal 140 is a separate computing device such as, but not limited to, a desktop computer, a laptop computer, a tablet computer, and a smartphone.

Each component of system 100 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Figure 2A:
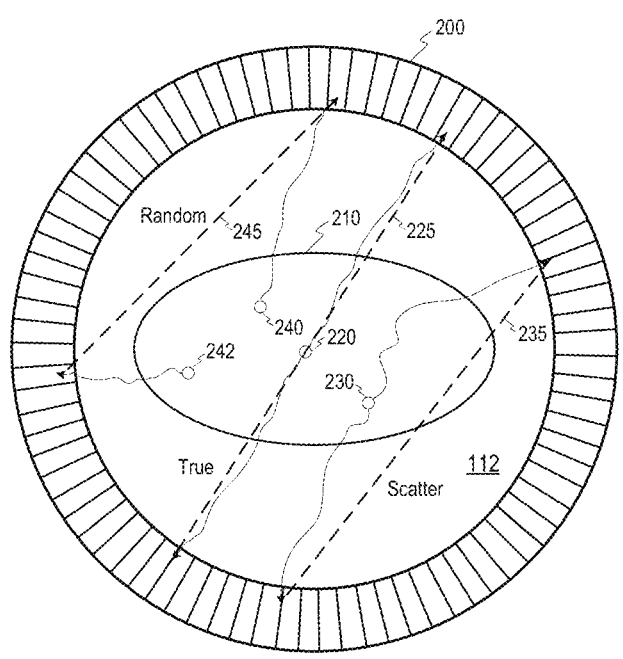
FIGS. 2a and 2b illustrate detection of coincidence events according to some embodiments.
Figure 2B:
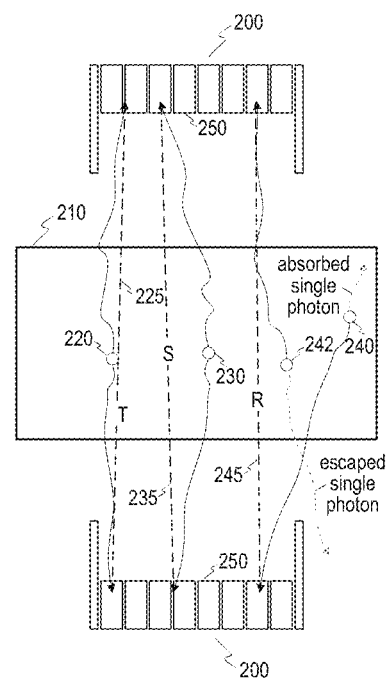

FIG. 2a and FIG. 2b illustrate detection of coincidence events according to some embodiments. FIG. 2a is an axial view of bore 112 of gantry 110 and imaging subject 210 disposed therein. Imaging subject 210 may comprise a human body, a phantom, or any other suitable subject. As shown, detector ring 200 surrounds imaging subject 210.

FIG. 2b is a transaxial view of detector ring 200 and body 210 of FIG. 2a. Detector ring 200 is composed of eight adjacent and coaxial rings of detectors 250 in the illustrated example. As will be described below, each detector 250 may comprise any number of scintillator crystals and electrical transducers.

Annihilation events 220, 230, 240 and 242 are assumed to occur at various locations within subject 210. As described above, an injected tracer generates positrons which are annihilated by electrons to produce two 511 keV photons which travel in approximately opposite directions. Each represented annihilation event results in the detection of a coincidence. True coincidences represent valid image data, while scatter and random coincidences represent noise associated with incorrect event position information.

A coincidence is detected when a pair of scintillation crystals receive two annihilation photons within the coincidence time window. Event 220 is associated with a true coincidence because event 220 resulted in two photons which were received within the coincidence time window and because the position of annihilation event 220 lies on LOR 225 connecting the detector positions at which the two photons were received.

Event 230 is associated with a scatter coincidence because, even though the two photons resulting from event 230 were detected within the coincidence time window, the position of annihilation event 230 does not lie on LOR 235 connecting the two photon positions. This may be due to Compton (i.e., inelastic) or Coherent (i.e., elastic) scatter resulting in a change of direction of at least one of the two annihilation photons within subject 210.

Events 240 and 242 are two separate annihilation events which result in detection of a random coincidence. In the present example, one of the photons generated by event 240 is absorbed in body 210 and one of the photons generated by event 242 escapes detection by any detector 250 of detector ring 200. The remaining photons happen to be detected within the coincidence time window, even though no annihilation event occurred on LOR 245 connecting the positions at which the coincident photons were received.

Figure 3:
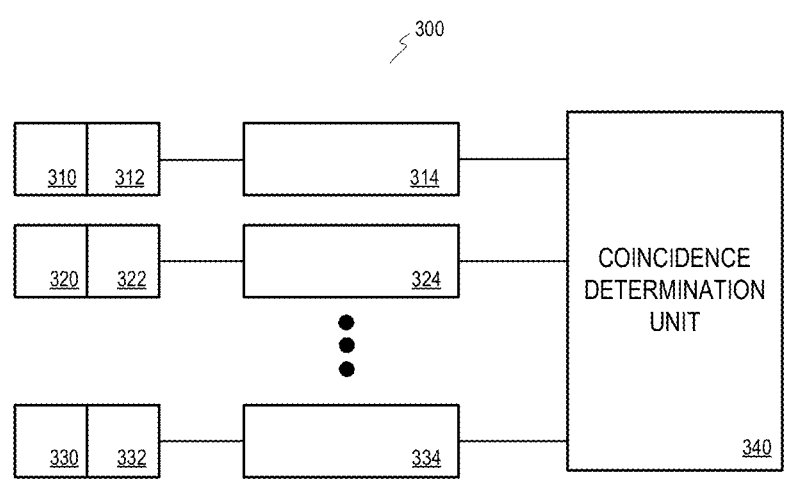
FIG. 3 is a block diagram of a coincidence detection system according to some embodiments.

FIG. 3 is a block diagram of coincidence detection system 300 according to some embodiments. System 300 includes scintillation units 310, 320 and 330, respective electrical transducer units 312, 322 and 332, and respective signal processing components 314, 324 and 334. Coincidence determination unit 340 receives signals from each of signal processing components 314, 324 and 334.

Each of scintillation units 310, 320 and 330 may include one or more scintillation crystals. For example, each of scintillation units 310, 320 and 330 may comprise a mini-block of 5×5 crystal elements, a macro-block of 2×2 mini-blocks, or a detector composed of two macro-blocks. Embodiments are not limited to any particular configuration or construction of scintillation units 310, 320 and 330.

Each of electrical transducer units 312, 322 and 332 may comprise one or more PMTs, SiPMs or the like. The number of electrical transducers in each of units 312, 322 and 332 may be less than, equal to, or greater than the number of crystal elements in each of scintillation units 310, 320 and 330. According to some embodiments, an electrical transducer unit includes one 4×4 array of SiPMs for each mini-block of 5×5 crystal elements in its corresponding scintillation unit.

Signal processing components 314, 324 and 334 receive electrical signals from respective electrical transducer units 312, 322 and 332 and perform signal processing to, for example, determine whether a signal represents a photon detection event, perform signal unpiling by pile-up rejection and/or correction methods, and associate photon detection events with specific detector crystals of scintillation units 310, 320 and 330. Signal processing components 314, 324 and 334 may perform any suitable functions and exhibit any suitable implementations.

Coincidence determination unit 340 receives all photon detection events which pass energy qualification, called singles, and identifies pairs of events which occurred within a coincidence time window. The unit outputs a true coincidence event, random coincidence event or non-event. If the output is a true or random coincidence, each identified pair represents a coincidence and is associated with the two detector crystals associated with the pair of photon detection events.

Figure 4:
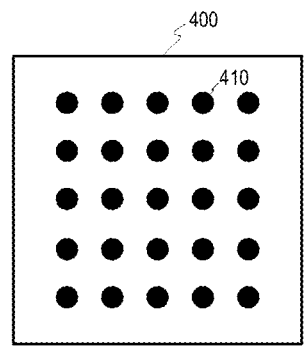
FIG. 4 illustrates a detector mini-block according to some embodiments.

FIG. 4 illustrates mini-block 400 of crystals according to some embodiments. In one example, mini-block 400 comprises a grid of 5×5 LSO crystals having dimensions of 3.2 mm×3.2 mm×20 mm. Mini-block 400 may be coupled to a 4×4 array of SiPMs for receiving light photons therefrom and generating electrical signals based thereon. Embodiments are not limited to the above description of mini-block 400.

Figure 5:
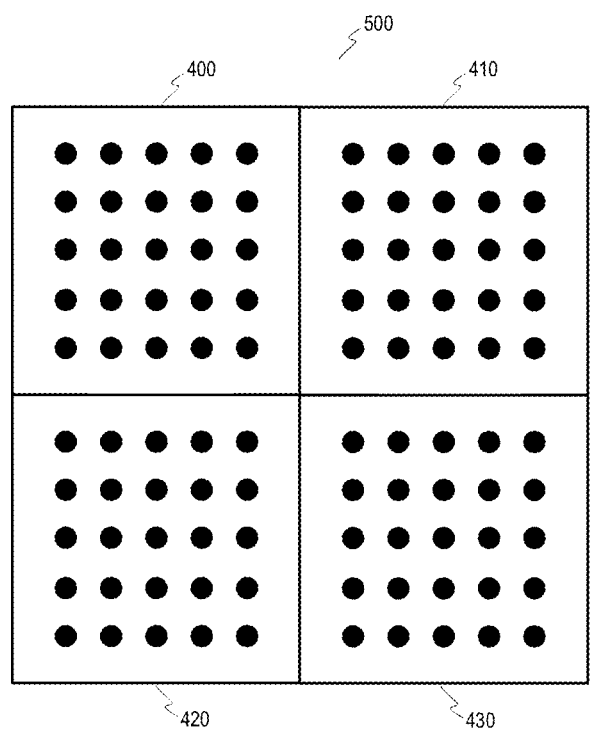
FIG. 5 illustrates a detector macro-block according to some embodiments.

FIG. 5 illustrates macro-block 500 according to some embodiments. Macro-block 500 is composed of mini-blocks 400, 410, 420 and 430, each of which may share the configuration of mini-block 400 of FIG. 4. According to non-exhaustive embodiments, a detector is composed of two macro-blocks disposed in the transaxial direction of a detector ring.

Figure 6:
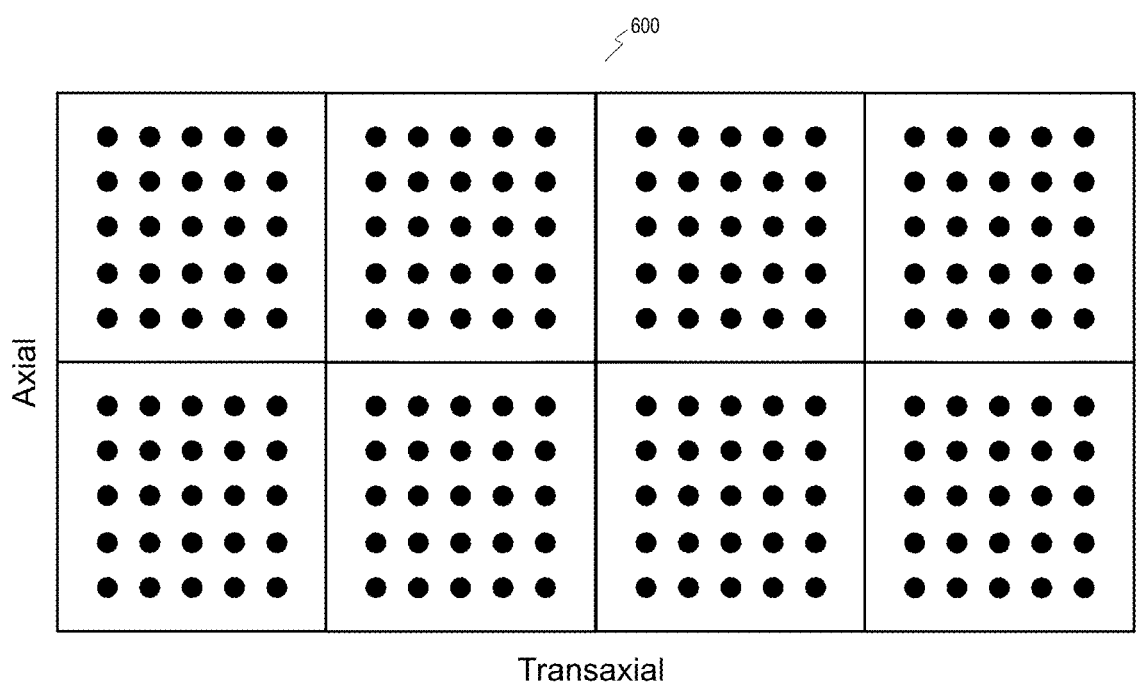
FIG. 6 illustrates a detector according to some embodiments.

FIG. 6 illustrates a detector according to some embodiments. Detector 600 includes two macro-blocks in the transaxial direction. Accordingly, detector 600 consists of eight mini-block, with two mini-blocks in the axial direction and four mini-blocks in the transaxial direction. Detector 600 therefore includes 200 crystals, with rows of 10 crystals in the axial direction and 20 crystals in the transaxial direction.

Figure 7:
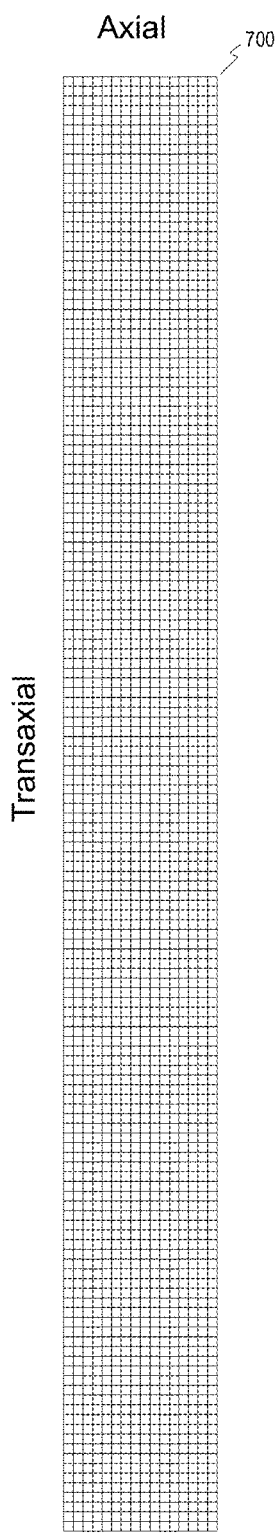
FIG. 7 illustrates detector rings of a PET scanner according to some embodiments.

FIG. 7 represents PET scanner 700 according to some embodiments. PET scanner 700 may be deployed within a scanner gantry in a ring-like configuration as depicted in FIG. 2a, and is presented in an "unrolled" manner in FIG. 7 for clarity.

Scanner 700 includes 8 detectors in the axial direction and 38 detectors in the transaxial direction. As such, scanner 700 includes 16 mini-blocks in the axial direction and 152 mini-blocks in the transaxial direction. According to the present example, scanner 700 therefore includes 60800 detector crystals, with rows of 80 detector crystals in the axial direction and rows of 760 detector crystals in the transaxial direction. Embodiments are not limited to the specific structure or components of scanner 700.

Figure 8:
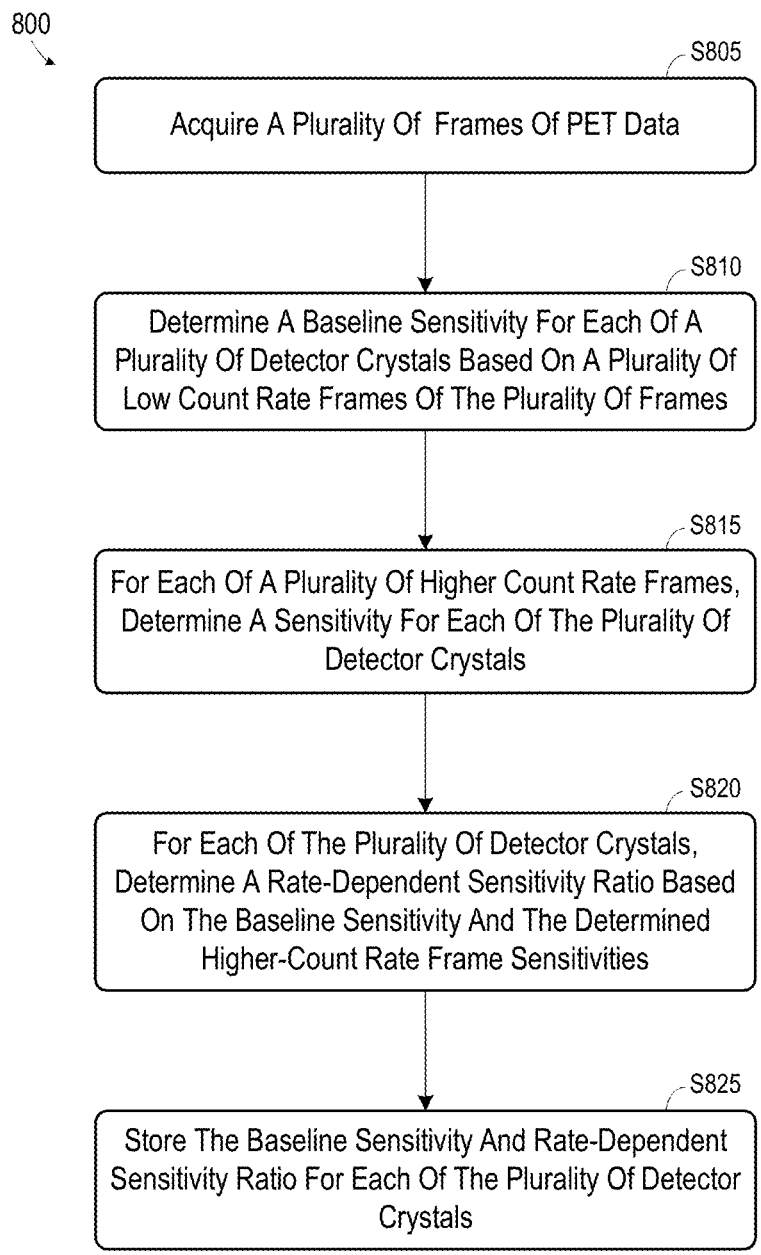
FIG. 8 comprises a flow diagram of a process to determine baseline sensitivities and rate-dependent sensitivity ratios of detector crystals according to some embodiments.

FIG. 8 comprises a flow diagram of process 800 to determine baseline sensitivities and rate-dependent sensitivity ratios according to some embodiments. As mentioned above and to be described in further detail below, the baseline sensitivities and rate-dependent sensitivity ratios may be used to estimate the mean random coincidence rates for pairs of crystals for a given acquired PET frame. The mean random coincidence rates may be used to correct the PET frame prior to image reconstruction.

Flow diagram 800 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

A plurality of PET frames are acquired at S805. The PET frames may be acquired by a conventional static PET scan after injection of a radionuclide tracer into a volume as is known in the art. According to some embodiments, the volume comprises a phantom such as, for example, a uniform water-filled cylinder. The radionuclide tracer may comprise any suitable tracer, such as but not limited to FDG. According to some embodiments, the volume and the tracer used at S805 are selected to correspond to a volume and tracer of a future PET scan, where the data acquired by the future PET scan is to be corrected based on the baseline sensitivities and rate-dependent sensitivity ratios determined during subsequent steps of process 800.

The acquired PET frames may comprise, in some embodiments, list-mode PET data as described above. The PET frames may be acquired by an imaging system separate from a system to perform the remainder of process 800. For example, the PET frames may have been originally acquired in an imaging theatre, with the remainder of process 800 being executed by a separate computing system in a separate location hours, days, months, etc. after the acquisition.

Figure 9:
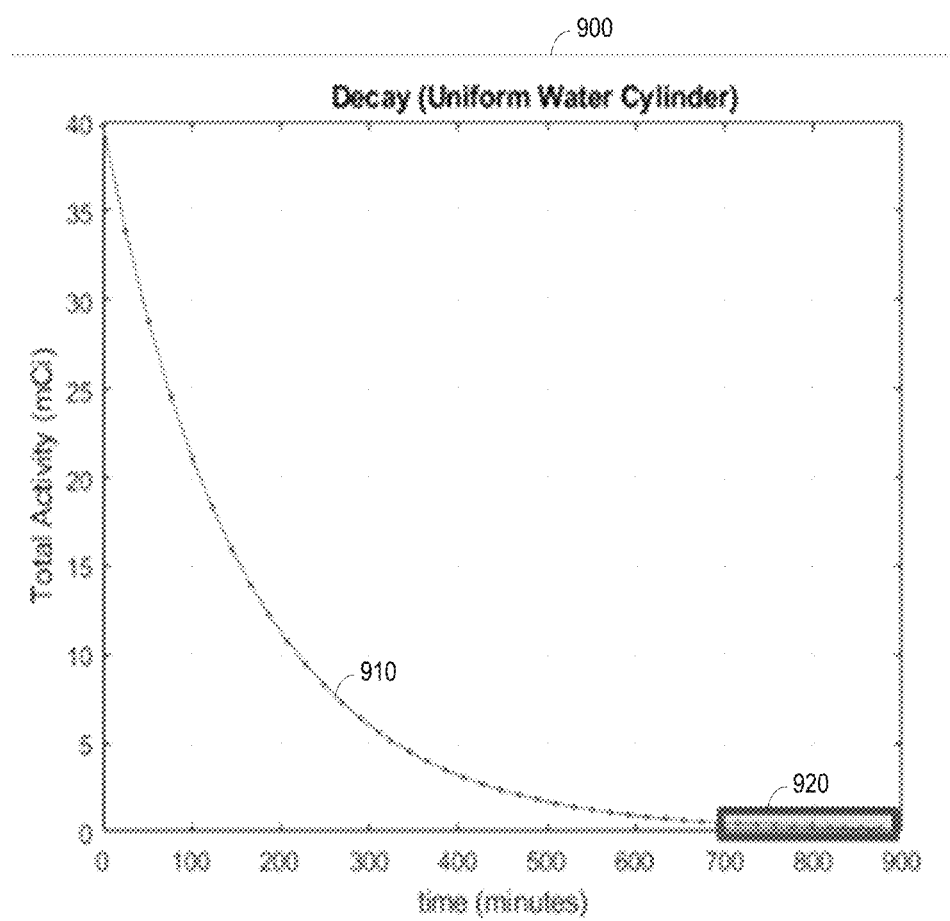
FIG. 9 is a graph of activity versus time for determining frame rates for acquired calibration frames according to some embodiments.

FIG. 9 illustrates graph 900 of tracer activity versus time during acquisition of PET frames at S805 according to some embodiments. The total tracer activity is greatest immediately after injection (i.e., at 0 minutes) and decreases thereafter. Each distinctly-represented point of curve 910 represents acquisition of one PET frame. Each PET frame therefore represents coincidences detected between the time of the frame acquisition and the acquisition time of an immediately-prior PET frame.

A baseline sensitivity for each of a plurality of detector crystals is determined at S810. The baseline sensitivities are determined based on a plurality of low count rate frames of the acquired plurality of PET frames. For purposes of the present example, it will be assumed that the baseline sensitivities are determined based on the low count rate frames indicated by box 920 of graph 900.

For example, for each of the low count rate PET frames, a number of coincidence detection events associated with each crystal of a detector is determined based on the frame data. Because the detector count rates are close to one another, the number of coincidence detection events associated with each crystal of a detector for each of the low count frames is averaged. The number of events associated with each crystal is then normalized based on the number of events associated with each other crystal, resulting in a baseline sensitivity for each crystal. An average baseline sensitivity of each crystal may then be determined based on the baseline sensitivities of each crystal determined from each of the low count rate PET frames.

Figure 10:
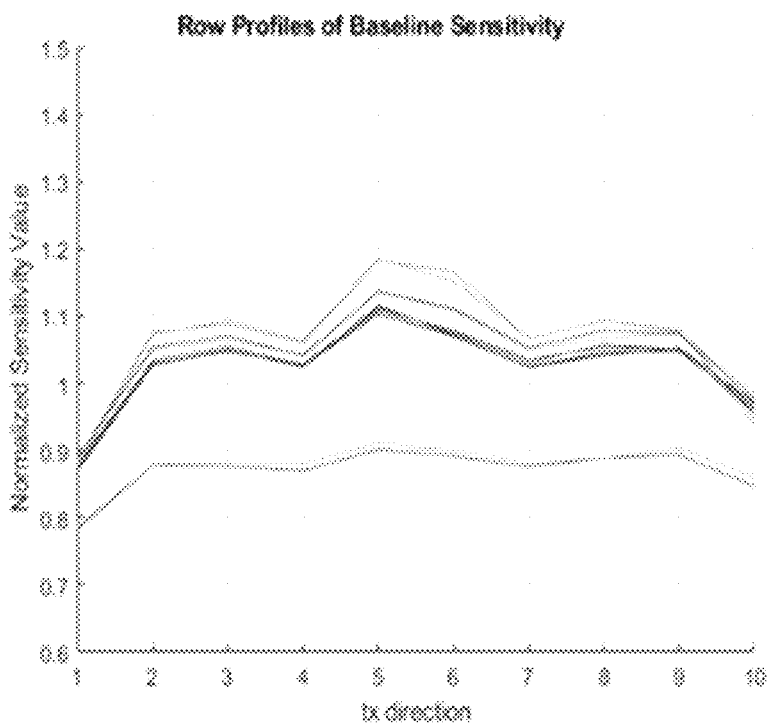
FIG. 10 is a graph of baseline sensitivities for each crystal of a detector macro-block according to some embodiments.

FIG. 10 is a graph of baseline sensitivities determined at S810 for one macro-block of 10×10 crystals. Each graphed line represents a single axial position (i.e., a row of crystals in the transaxial direction) of the macro-block, and the baseline sensitivity of crystals located at each transaxial position of the axial position.

Figure 11:
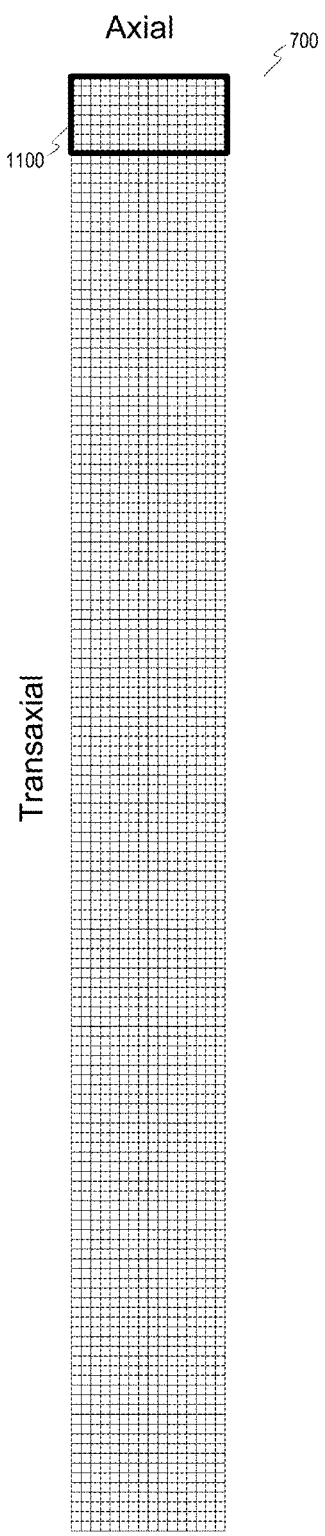
FIG. 11 illustrates a group of detectors for which crystal baseline sensitivities and rate-dependent sensitivity ratios are determined according to some embodiments.

According to some embodiments, S810 includes determination of baseline sensitivities for a subset of detectors/crystals of the entire PET scanner. For example, S810 may include determination of baseline sensitivities for a 4×4 array of detectors such as detectors 1100 of FIG. 11. According to this example, baseline sensitivities are determined for 40×80=3200 crystals. As will be described below, the symmetry of scanner 700 may be leveraged to map the baseline sensitivities (and rate-dependent sensitivity ratios) of the 3200 crystals to corresponding ones of the other 57600 crystals of scanner 700.

A sensitivity for each of the plurality of detector crystals is determined at S815 for each of a plurality of higher count rate frames. For example, a number of coincidence detections associated with each of the plurality of detector crystals is determined based on the frame data of one of the high count rate PET frames represented by graph 900 and acquired at a time between 0 and 200 minutes. The number of events associated with each crystal is then normalized based on the number of events associated with each other crystal, to determine a sensitivity value for each crystal.

Figure 12:
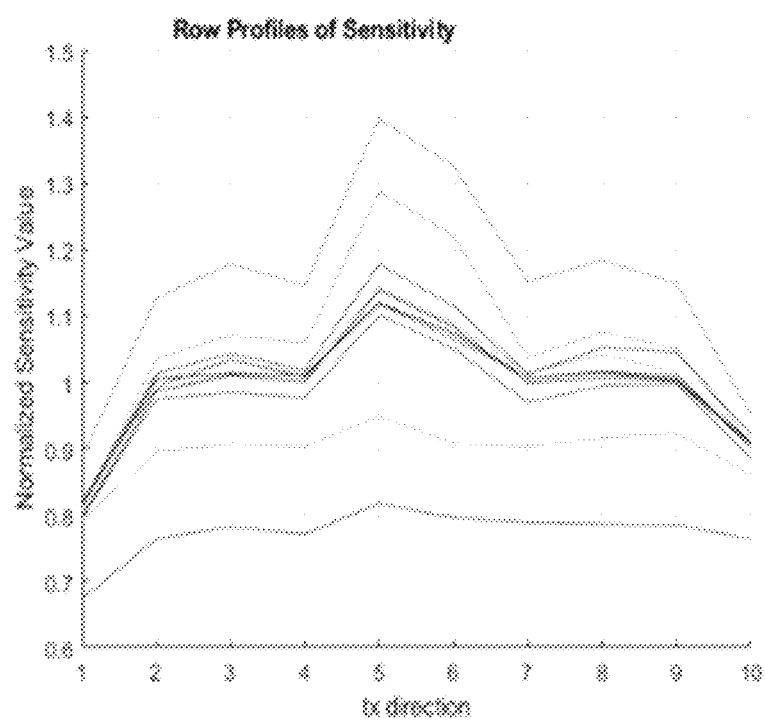
FIG. 12 is a graph of high rate sensitivities for each crystal of a detector macro-block according to some embodiments.

FIG. 12 is a graph of sensitivity profiles determined at S815 for one macro-block of 10×10 crystals based on one high count rate frame. Each graphed line represents a single axial position of the macro-block, and the sensitivity of crystals located at each transaxial position of the axial position. The foregoing process is repeated for one or more other high count rate PET frames (e.g., acquired at a time between 0 and 200 minutes), resulting in a plurality of sensitivities associated with each crystal. Each of the plurality of sensitivities associated with a crystal is also associated with a count rate (i.e., the count rate of the frame used at S815 to determine the sensitivity).

Figure 13:
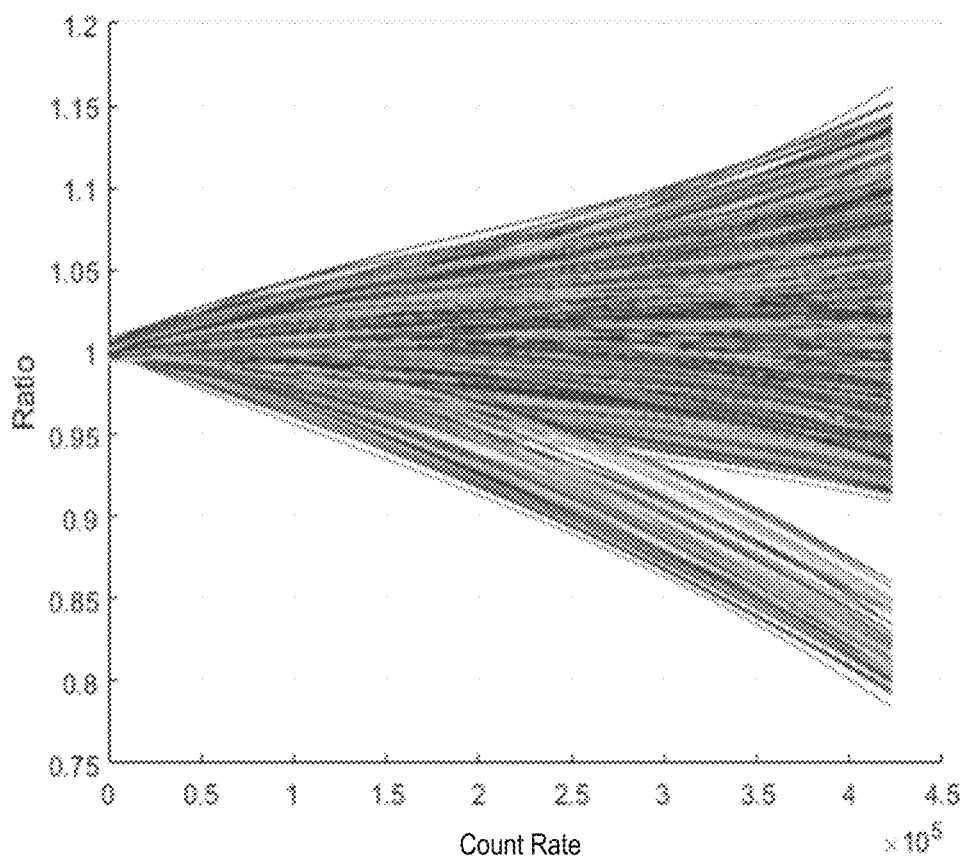
FIG. 13 is a graph of rate-dependent detector crystal sensitivity ratios according to some embodiments.

Next, at S820, a rate-dependent sensitivity ratio for each detector crystal is determined based on the baseline sensitivity and the sensitivities determined for the crystal at S815. In one example of S820, and for each crystal, a sensitivity ratio for a given count rate is determined by dividing the sensitivity associated with the given count rate and the crystal by the baseline sensitivity of the crystal. Similar ratios are determined for sensitivities associated with each other count rate. All determined ratios may then be plotted against their corresponding count rates to determine a rate-dependent sensitivity ratio for the detector crystal. FIG. 13 is a graph of sensitivity ratios versus detector count rate. Each line of the FIG. 13 graph represents a rate-dependent sensitivity ratio of all crystals of a single detector.

The baseline sensitivity and rate-dependent sensitivity ratio of each of the plurality of detector crystals are stored at S825. The stored baseline sensitivities and rate-dependent sensitivity ratios may be used to estimate mean random coincidences for each pair of detector crystals within subsequently-acquired PET data according to some embodiments. As described above, symmetries of a PET scanner may be exploited to map each of the stored baseline sensitivities and rate-dependent sensitivity ratios to more than one crystal of the scanner.

Figure 14:
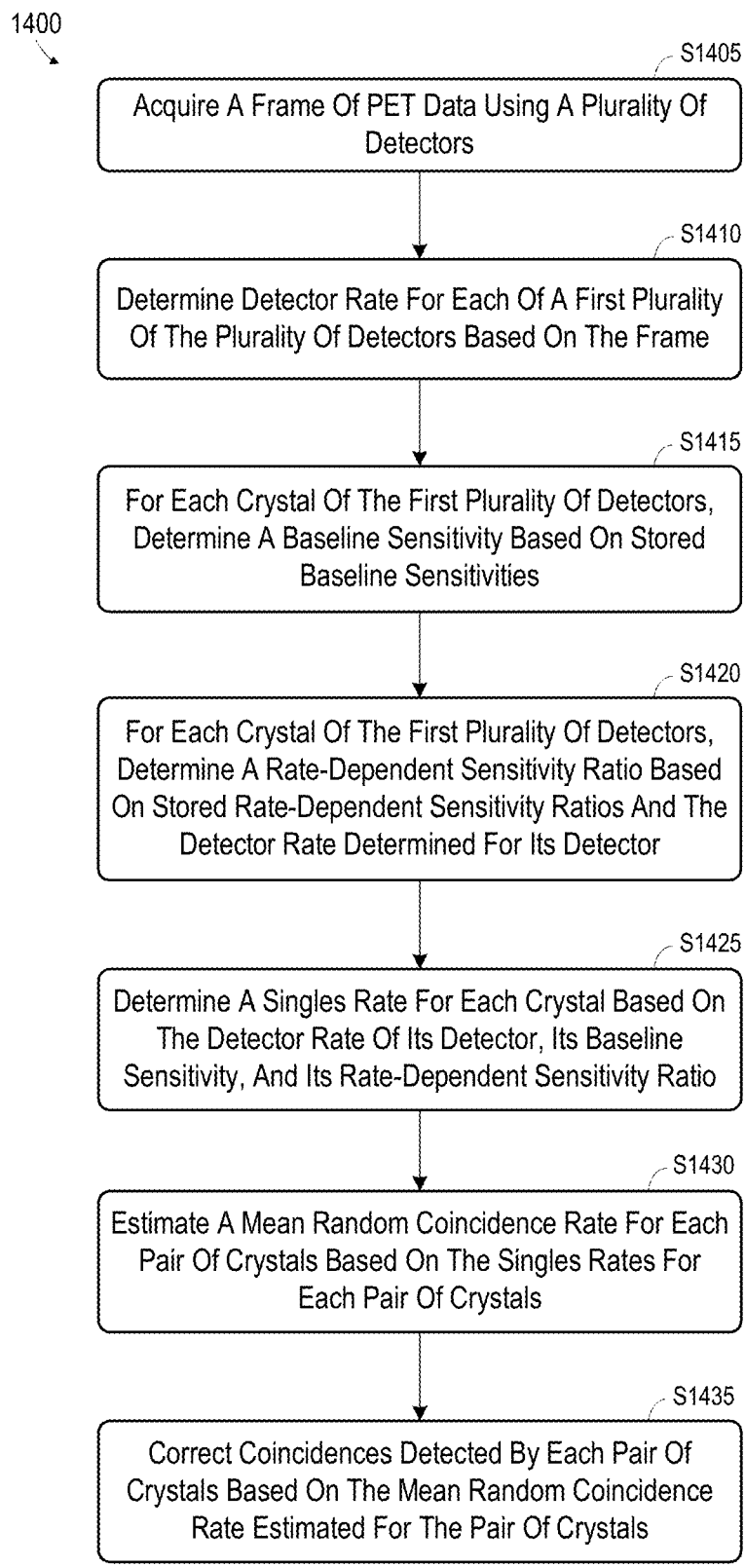
FIG. 14 comprises a flow diagram of a process to estimate a mean random coincidence rate and correct coincidence data using baseline sensitivities and rate-dependent sensitivity ratios of detector crystals according to some embodiments.

FIG. 14 is a flow diagram of process 1400 to determine a mean random coincidence rate for a pair of detector crystals according to some embodiments. Process 1400 assumes the availability of a baseline sensitivity value and rate-dependent sensitivity ratio for each detector crystal of each pair for which the random coincidence rate is to be determined.

A frame of PET data is acquired at S1405 using a plurality of detectors. The plurality of detectors may comprise all the detectors of a scanner as depicted in FIGS. 2a, 2b and 7. The frame of PET data may be acquired at S1405 by detecting coincidences emitted from a volume of interest such as a human patient over a period of time. The acquired frame may comprise list-mode data or sinograms specifying all detected coincidences and a pair of detector crystals associated with each coincidence.

A detector rate is determined for each of the plurality of detectors at S1410. The detector rate is determined based on the frame of PET data, and represents a rate at which a detector received valid (i.e., energy-qualified) photons during acquisition of the frame. For example, a header of the frame of PET data may indicate a detector rate for each detector of the PET scanner.

Next, at S1415, a baseline sensitivity is determined for each crystal of the first plurality of detectors. The baseline sensitivity may be determined based on pre-stored baseline sensitivities. In some embodiments, a baseline sensitivity for each crystal in a scanner is pre-determined and pre-stored, and such baseline sensitivities are simply read at S1415. According to other embodiments, baseline sensitivities are pre-stored for only a subset of detector crystals, and these baseline sensitivities are mapped to all other detector crystals in the scanner based on physical symmetries of the scanner.

Similarly, at S1420, a rate-dependent sensitivity ratio is determined for each crystal of the first plurality of detectors. The rate-dependent sensitivity ratio may be determined based on pre-stored rate-dependent sensitivity ratios. A rate-dependent sensitivity ratio for each crystal may be pre-determined and pre-stored, or ratios may be pre-stored for only a subset of detector crystals, and mapped to all other detector crystals in the scanner based on physical symmetries of the scanner.

A singles rate for each crystal is determined at S1425. The singles rate of a crystal is determined based on the detector rate of the detector to which the crystal belongs, the baseline sensitivity of the crystal, and the rate-dependent sensitivity ratio of the crystal.

Generally, S1425 operates to apportion the detector rate of a detector for a given frame among the crystals of the detector based on respective crystal sensitivities, as opposed to evenly. More specifically, a sensitivity ratio for each crystal of a given detector is determined based on the detector rate determined for the given detector at S1410 and the rate-dependent sensitivity ratio of the crystal. A sensitivity for each crystal is then determined by multiplying its baseline sensitivity with its sensitivity ratio. The detector rate of the detector is then apportioned to each crystal based on each crystal's sensitivity. The rate apportioned to a given crystal is considered to be the singles rate of the given crystal for the acquired frame.

The following equation represents determination of the singles rate for each crystal of a detector according to some embodiments.

$$S_{t_x a_x} = b_{ij} \times \frac{f_{ij}(r_{t_x a_x})}{\sum_{ij} b_{ij} f_{ij}(r_{t_x a_x})} \times r_{t_x a_x},$$

where
$t_x$: transaxial crystal index
$a_x$: axial crystal index $$i = \text{remainder}\left(\frac{t_x}{n_x}\right):$$

transaxial crystal index in the model domain
$j=a_x$: axial crystal index in the model domain
$n_x$: number of crystals in the transaxial direction in one detector module (e.g., $n_x=20$)
$b_{ij}$: baseline sensitivity
$f_{ij}(r_{t_x a_x})$: rate-dependent sensitivity ratio for crystal ($t_x$, $a_x$) in the scanner $r_{t_x a_x}$: measured block (detector) rates for crystal ($t_x$, $a_x$) in the scanner $S_{t_x a_x}$: the crystal singles rates for the scanner Determination of the singles rate for a given crystal according to some embodiments utilizes a pre-stored rate-dependent sensitivity ratio and baseline sensitivity for the given crystal. In order to avoid storage of a separate rate-dependent sensitivity ratio and baseline sensitivity for each crystal (e.g., 57600 crystals) symmetry of the scanner is exploited to map more than one crystal to a single pre-stored rate-dependent sensitivity ratio and baseline sensitivity. According to some embodiments, each crystal of 152 (transaxial)×16 (axial) mini-blocks of a scanner is mapped to a respective crystal of 8 (transaxial)×16 (axial) mini-blocks. In such an embodiment, each pre-stored rate-dependent sensitivity ratio and baseline sensitivity is mapped to 19 different crystals.

A mean random coincidence rate is determined for each pair of crystals at S1430. The mean random coincidence rate is determined based on the singles rate determined for each detector crystal of each pair of detector crystals. According to some embodiments, the mean random coincidence rate for a pair of detector crystals is estimated at S1430 using the formula below.

$$\overline{R_{ij}} = 2\tau S_{t1_x a1_x} S_{t2_x a2_x}$$

where
$\overline{R_{ij}}$: estimated mean random coincidence rate for a pair of crystals ($t1_x$, $a1_x$) and ($t2_x$, $a2_x$)
$S_{t1_x a1_x}$: the singles rate for crystal ($t1_x$, $a1_x$)
$t1_x$: transaxial crystal index
$a1_x$: axial crystal index
$2\tau$: the coincidence time window At S1435, the coincidences of the acquired PET frame are corrected based on the mean random coincidence rate determined for each pair of detector crystals. According to some embodiments, all coincidences detected by a particular pair of detector crystals are identified in the acquired PET frame. A number of random coincidences associated with each particular pair of detector crystals is then determined based on the mean random coincidence rate determined for each pair of detector crystals as is known in the art.

For example, the number of random coincidences associated with each particular pair of detector crystals over a frame interval may be determined based on a Poisson distribution:

$$P(x) = \frac{\overline{R_{ij}}^x e^{-\overline{R_{ij}}}}{x!}$$

where $\overline{R_{ij}}$ is the mean random coincidence rate for a given crystal pair over the frame interval (i.e., the mean random coincidence rate multiplied by the frame interval). x corresponds to an estimated quantized value of random coincidences based on a Poisson probability distribution. Accordingly, x is analogous to the measured random counts in the above-described delayed logic method and may be used to correct the acquired coincidence data for random coincidences. For example, the total number of detected coincidences associated with a given crystal pair is reduced based on the value of x determined for the given crystal pair.

A PET image may be reconstructed from the corrected PET data. Such a PET image may exhibit less noise than an image reconstructed from non-corrected PET data, and may exhibit a greater signal-to-noise ratio than an image reconstructed from PET data subjected to random correction based on delayed coincidence techniques.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a positron emission tomography scanner comprising a plurality of detectors, each of the plurality of detectors comprising a plurality of detector crystals, the positron emission tomography scanner to acquire a frame of positron emission tomography data; and
   a processing unit to:
   determine a detector rate for each of the plurality of detectors based on the frame of positron emission tomography data;
   for each detector crystal of the plurality of detectors, determine a sensitivity based on the detector rate of the detector including the detector crystal;
   for each detector crystal, determine a singles rate based on the detector rate of the detector including the detector crystal and the determined sensitivity of the detector crystal;
   estimate a mean random coincidence rate for each of a plurality of pairs of the detector crystals based on the singles rate of each detector crystal of each of the plurality of pairs of the detector crystals; and
   correct the acquired frame of positron emission tomography data based on the estimated mean random coincidence rates.

2. A system according to claim 1, wherein determination of the sensitivity for each detector crystal of the plurality of detectors comprises:
   determination of a baseline sensitivity for each detector crystal of the plurality of detectors;
   determination of a rate-dependent sensitivity ratio for each detector crystal of the plurality of detectors; and
   determination of the sensitivity for each detector crystal, based on the detector rate of the detector including the detector crystal, the baseline sensitivity for the detector crystal and the rate-dependent sensitivity ratio for the detector crystal.

3. A system according to claim 2, wherein determination of the sensitivity of a detector crystal comprises:
   determination of a sensitivity ratio based on the detector rate of the detector including the detector crystal and the rate-dependent sensitivity ratio for the detector crystal; and
   determination of a product of the baseline sensitivity determined for the detector crystal and the sensitivity ratio determined for the detector crystal.

4. A system according to claim 3, wherein determination of the singles rate of a detector crystal comprises apportioning the detector rate of the detector including the detector crystal based on the sensitivity of the detector crystal and the sensitivity of other detector crystals of the detector including the crystal.

5. A system according to claim 1, wherein determination of the sensitivity comprises determination of the sensitivity based on the detector rate of the detector including the detector crystal and on a rate-dependent sensitivity ratio associated with the detector crystal.

6. A system according to claim 1,
   the positron emission tomography scanner to acquire a second frame of positron emission tomography data; and
   the processing unit to:
   determine a second detector rate for each of the plurality of detectors based on the second frame of positron emission tomography data;
   for each detector crystal of the plurality of detectors, determine a second sensitivity based on the second detector rate of the detector including the detector crystal;
   for each detector crystal, determine a second singles rate based on the second detector rate of the detector including the detector crystal and the determined second sensitivity of the detector crystal;
   estimate a second mean random coincidence rate for each of the plurality of pairs of the detector crystals based on the second singles rate of each detector crystal of each of the plurality of pairs of the detector crystals; and
   correct the acquired second frame of positron emission tomography data based on the estimated second mean random coincidence rates.

7. A system according to claim 6, the processing unit to:
   reconstruct a positron emission tomography image based on the corrected first frame of positron emission tomography data and the corrected second frame of positron emission tomography data.

8. A method comprising:
   acquiring a frame of positron emission tomography data; and
   determining a detector rate for each of a plurality of detectors of a positron emission tomography scanner based on the frame of positron emission tomography data, each of the plurality of detectors comprising a plurality of detector crystals;
   determining, for each detector crystal of the plurality of detectors, a sensitivity based on the detector rate of the detector including the detector crystal;
   determining, for each detector crystal, a singles rate based on the detector rate of the detector including the detector crystal and the determined sensitivity of the detector crystal;
   estimating a mean random coincidence rate for each of a plurality of pairs of the detector crystals based on the singles rate of each detector crystal of each of the plurality of pairs of the detector crystals;
   correcting the acquired frame of positron emission tomography data based on the estimated mean random coincidence rates; and
   reconstructing a positron emission tomography image based on the corrected frame of positron emission tomography data.

9. A method according to claim 8, wherein determining the sensitivity for each detector crystal of the plurality of detectors comprises:

determining a baseline sensitivity for each detector crystal of the plurality of detectors;

determining a rate-dependent sensitivity ratio for each detector crystal of the plurality of detectors; and determining the sensitivity for each detector crystal based on the detector rate of the detector including the detector crystal, the baseline sensitivity for the detector crystal and the rate-dependent sensitivity ratio for the detector crystal.

10. A method according to claim 9, wherein determining the sensitivity of a detector crystal comprises:

determining a sensitivity ratio based on the detector rate of the detector including the detector crystal and the rate-dependent sensitivity ratio for the detector crystal; and determining a product of the baseline sensitivity determined for the detector crystal and the sensitivity ratio determined for the detector crystal.

11. A method according to claim 10, wherein determining the singles rate of a detector crystal comprises apportioning the detector rate of the detector including the detector crystal based on the sensitivity of the detector crystal and the sensitivity of other detector crystals of the detector including the crystal.

12. A method according to claim 8, wherein determining the sensitivity comprises determination of the sensitivity based on the detector rate of the detector including the detector crystal and on a rate-dependent sensitivity ratio associated with the detector crystal.

13. A method according to claim 8, further comprising:

acquiring a second frame of positron emission tomography data;

determining a second detector rate for each of the plurality of detectors based on the second frame of positron emission tomography data;

for each detector crystal of the plurality of detectors, determining a second sensitivity based on the second detector rate of the detector including the detector crystal;

for each detector crystal, determining second singles rate based on the second detector rate of the detector including the detector crystal and the determined second sensitivity of the detector crystal;

estimating a second mean random coincidence rate for each of the plurality of pairs of the detector crystals based on the second singles rate of each detector crystal of each of the plurality of pairs of the detector crystals; and correcting the acquired second frame of positron emission tomography data based on the estimated mean second random coincidence rates.

14. A method according to claim 8, further comprising:

reconstructing a second positron emission tomography image based on the corrected second frame of positron emission tomography data.

15. A computer-readable medium storing processor-executable process steps which when executed by a processing unit of a computing system, cause the computing system to:

determine a detector rate for each of a plurality of detectors of a positron emission tomography scanner based on a frame of positron emission tomography data, each of the plurality of detectors comprising a plurality of detector crystals;

determine a sensitivity for each detector crystal of the plurality of detectors, based on the detector rate of the detector including the detector crystal;

determine, for each detector crystal, a singles rate based on the detector rate of the detector including the detector crystal and the determined sensitivity of the detector crystal;

estimate a mean random coincidence rate for each of a plurality of pairs of the detector crystals based on the singles rate of each detector crystal of each of the plurality of pairs of the detector crystals;

correct the acquired frame of positron emission tomography data based on the estimated mean random coincidence rates; and reconstruct a positron emission tomography image based on the corrected frame of positron emission tomography data.

16. A computer-readable medium according to claim 15, wherein determination of the sensitivity for each detector crystal of the plurality of detectors comprises:

determination of a baseline sensitivity for each detector crystal of the plurality of detectors;

determination of a rate-dependent sensitivity ratio for each detector crystal of the plurality of detectors; and determination of the sensitivity for each detector crystal based on the detector rate of the detector including the detector crystal, the baseline sensitivity for the detector crystal and the rate-dependent sensitivity ratio for the detector crystal.

17. A computer-readable medium according to claim 16, wherein determination of the sensitivity of a detector crystal comprises:

determination of a sensitivity ratio based on the detector rate of the detector including the detector crystal and the rate-dependent sensitivity ratio for the detector crystal; and determination of a product of the baseline sensitivity determined for the detector crystal and the sensitivity ratio determined for the detector crystal.

18. A computer-readable medium according to claim 17, wherein determination of the singles rate of a detector crystal comprises apportionment of the detector rate of the detector including the detector crystal based on the sensitivity of the detector crystal and the sensitivity of other detector crystals of the detector including the crystal.

19. A computer-readable medium according to claim 15, wherein determination of the sensitivity comprises determination of the sensitivity based on the detector rate of the detector including the detector crystal and on a rate-dependent sensitivity ratio associated with the detector crystal.

20. A computer-readable medium according to claim 15, the processor-executable process steps which when executed by a processing unit of a computing system, further cause the computing system to:

acquire a second frame of positron emission tomography data;

determine a second detector rate for each of the plurality of detectors based on the second frame of positron emission tomography data;

for each detector crystal of the plurality of detectors, determine a second sensitivity based on the second detector rate of the detector including the detector crystal;

for each detector crystal, determine second singles rate based on the second detector rate of the detector including the detector crystal and the determined second sensitivity of the detector crystal;

estimate a second mean random coincidence rate for each of the plurality of pairs of the detector crystals based on the second singles rate of each detector crystal of each of the plurality of pairs of the detector crystals;

correct the acquired second frame of positron emission tomography data based on the estimated second mean random coincidence rates; and reconstruct a second positron emission tomography image based on the corrected second frame of positron emission tomography data.

* * * * *